Figure 1:
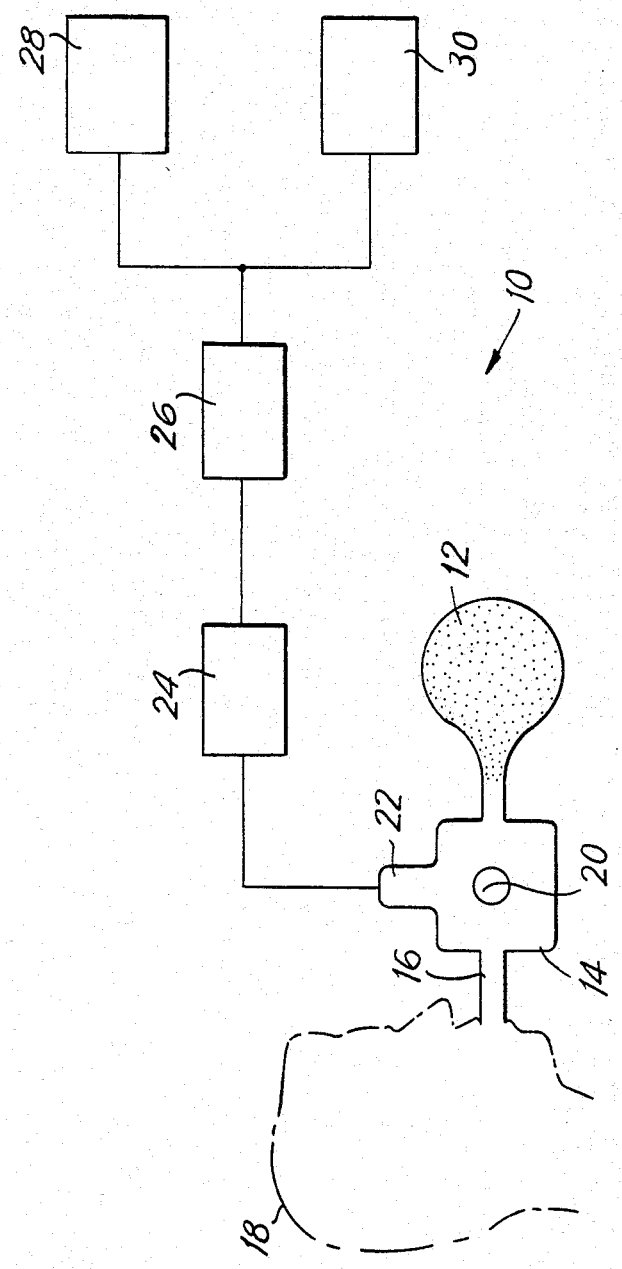
Figure 7:
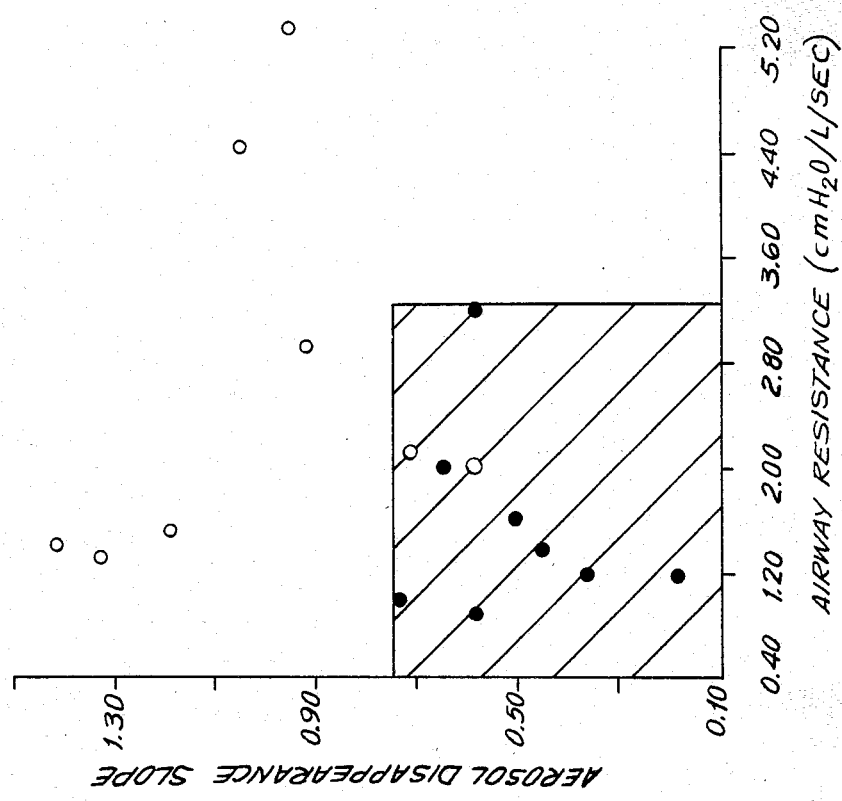
Figure 6:
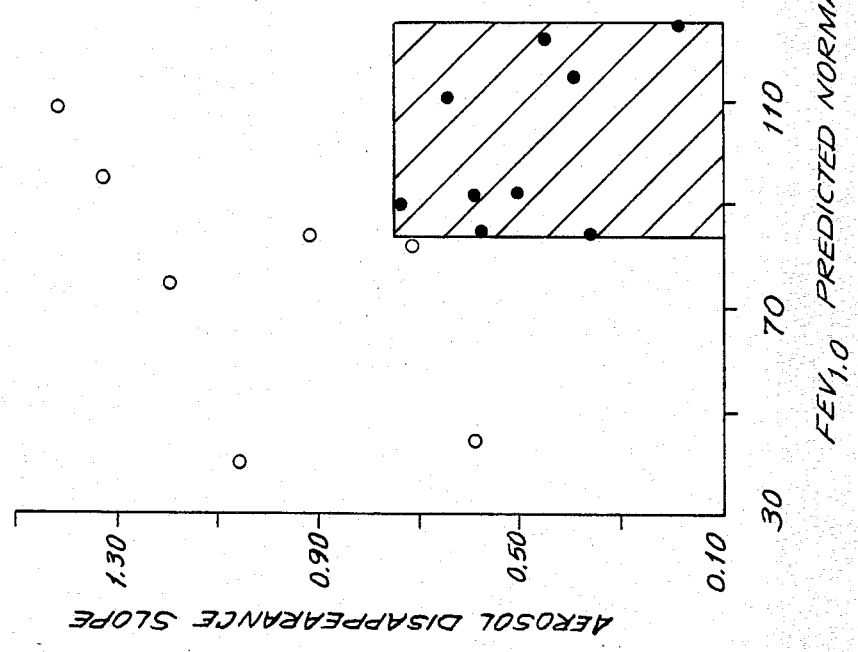

United States Patent [19]

Sackner et al.

[11] Patent Number: 4,517,987

[45] Date of Patent: May 21, 1985

[54] METHOD FOR MEASUREMENT OF NONRADIOISOTOPIC AEROSOL RETAINED IN THE LUNGS WITH RE-BREATHING

[76] Inventors: Marvin A. Sackner, 300 W. Rivo Alto Dr., Miami Beach, Fla. 33140; Chong S. Kim, 12040 SW. 112 Ave., Miami, Fla. 33176

[21] Appl. No.: 364,711

[22] Filed: Apr. 2, 1982

[51] Int. Cl.³ .............................................. A61B 5/08
[52] U.S. Cl. ..................................... 128/719; 422/84
[58] Field of Search ............... 128/716, 718, 719, 728, 128/730; 422/84

[56] References Cited

U.S. PATENT DOCUMENTS

| | | | |
|---|---|---|---|
| 3,527,205 | 9/1970 | Jones | 128/719 |
| 3,785,370 | 1/1974 | Richards et al. | 128/719 |
| 4,180,734 | 12/1979 | Gedeon | 128/719 X |
| 4,307,730 | 12/1981 | Korn | 128/728 |
| 4,370,986 | 2/1983 | Gebhart et al. | 128/716 |

OTHER PUBLICATIONS

Muir et al, "Distribution . . . Exhaled Air", J. App. Phys., vol. 23, No. 2, Aug. 1967, pp. 210-214.
Muir, "The Effect . . . Aerosol Curve", Airway Dynamics, pp. 319-325, 1970.
Taulbee et al, "Aerosol Transport . . . Single Breaths", Am. Phys. Society, pp. 803-812, 1978.
Clarke et al, "Resistance . . . Airways", J. App. Phys., vol. 29, No. 4, pp. 464-471, 1970.
Sackner et al, "Diffusing Capacity . . . Rebreathing Technique", Am. Review Resp. Disease, vol. III, 1975, pp. 157-165.
Taplin et al, "Early Detection of Chronic Obstructive . . . ", Chest, 71:5, May 1977, pp. 567-575.
Chopra et al, "Imaging Sites . . . Asthma", Thorax, 1979, 34, 493-500.
Emmett et al, "A New Apparatus . . . Breathing", J. Aerosol. Sci., vol. 10, No. 2, pp. 123-131, Mar. 1979.
Howerd et al, "Computerized Cardio. Pulmonary Stress . . . ", CH1480, 3/79, IEEE.
Altshuler et al, "Aerosol Deposition . . . Tract", A.M.A. Arch. Indus. Health, vol. 15, 1957, pp. 293-303.

*Primary Examiner*—Lee S. Cohen
*Attorney, Agent, or Firm*—Hubbell, Cohen, Stiefel & Gross

[57] ABSTRACT

A subject rebreathes an inert aerosol from a closed system and, during each of a plurality of breaths, the aerosol concentration in the closed system is determined and compared to determine differences with a predetermined concentration value. Identified differences indicating enhanced aerosol deposition signify airway narrowing and/or an increase in accumulated airway secretions.

5 Claims, 7 Drawing Figures

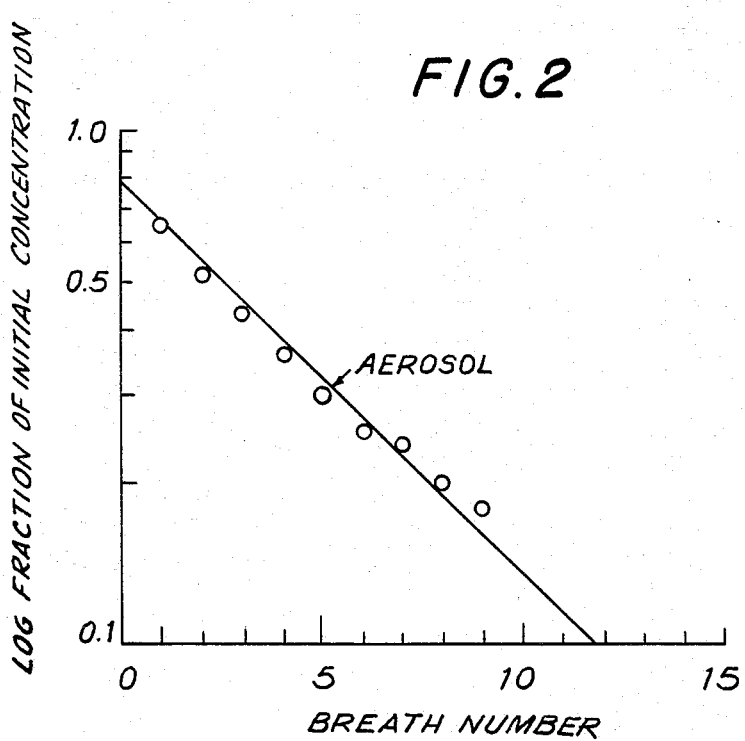
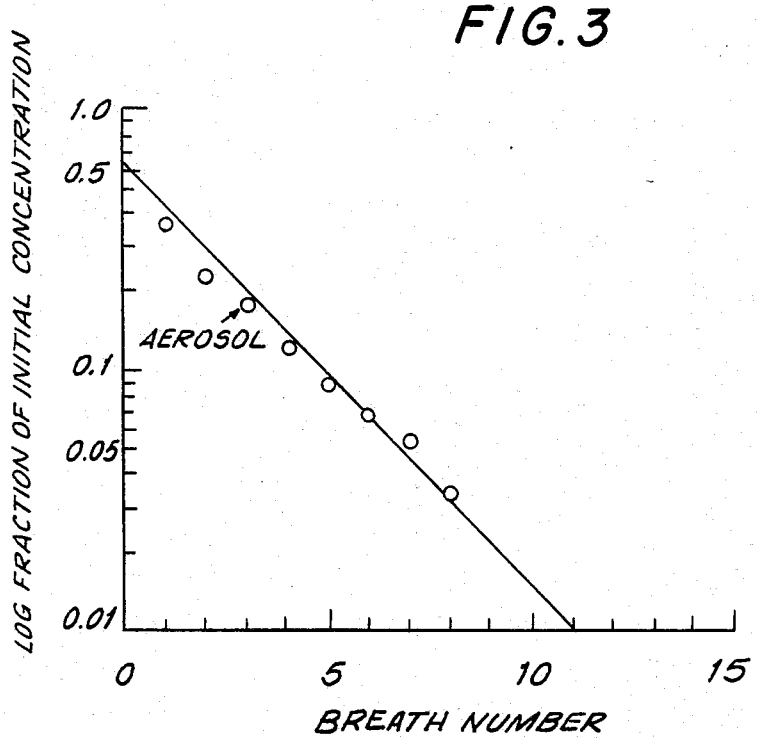

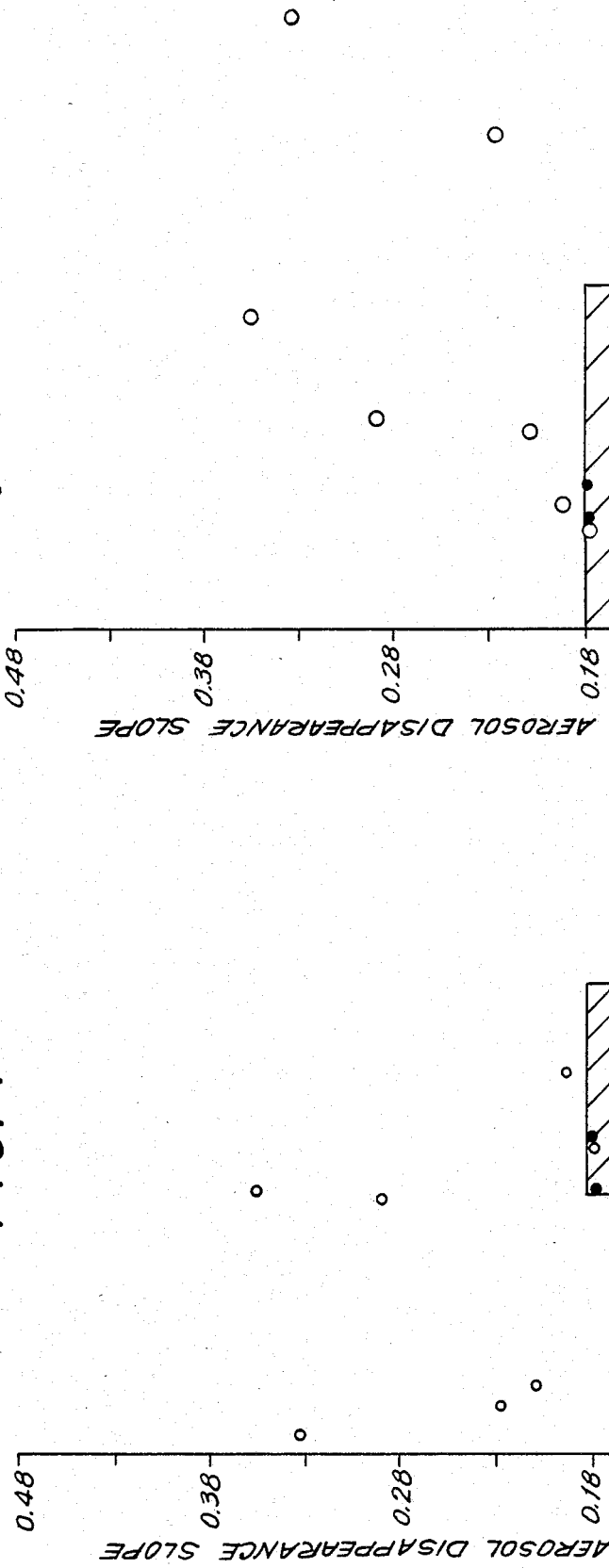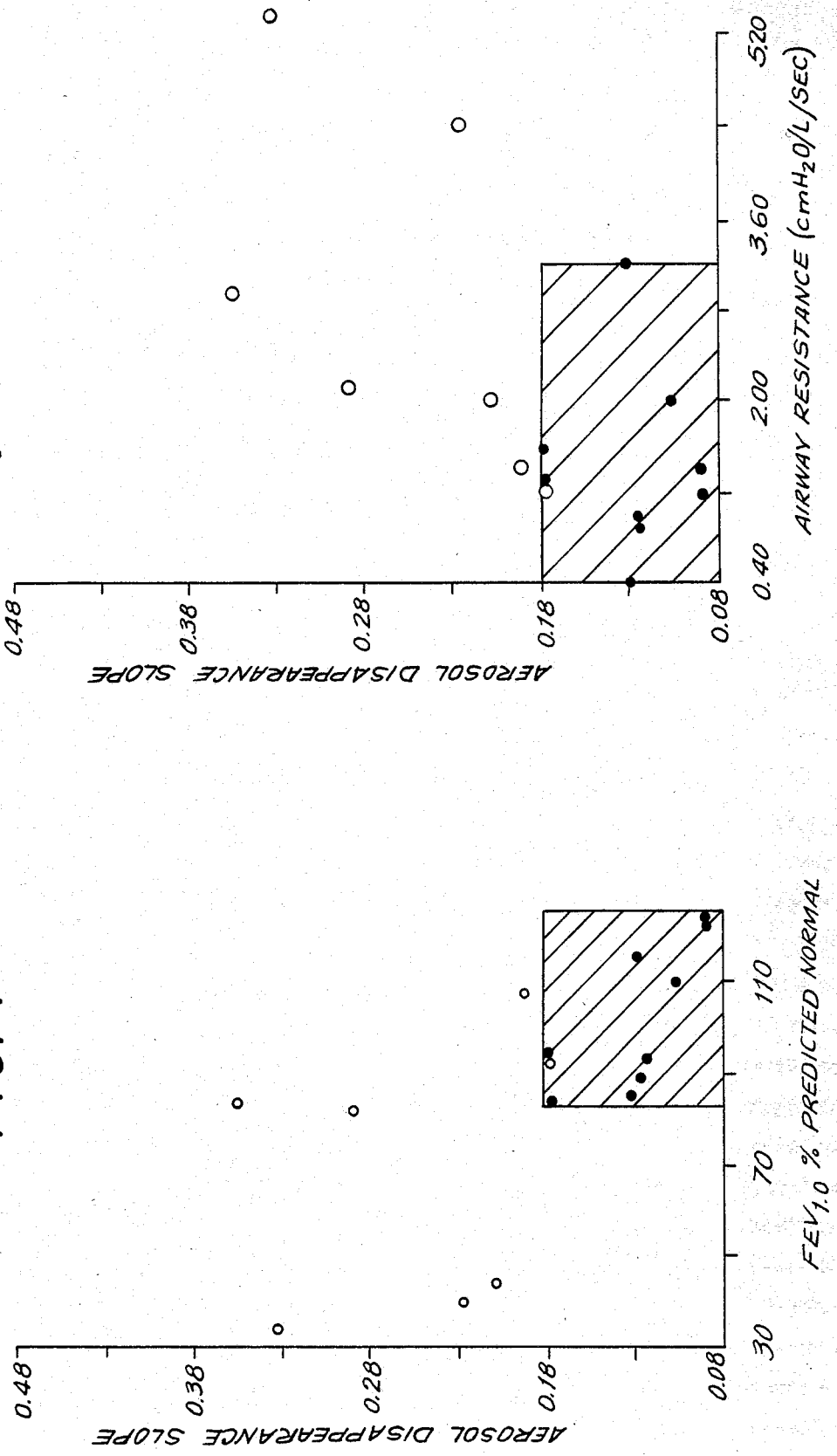

METHOD FOR MEASUREMENT OF NONRADIOISOTOPIC AEROSOL RETAINED IN THE LUNGS WITH RE-BREATHING

TECHNICAL FIELD

This invention pertains to a method for analyzing airway function by re-breathing an inert aerosol.

BACKGROUND ART

The prior art discloses numerous techniques for analyzing a subject's pulmonary function. In one such technique, the subject takes a single breath of an inert aerosol, and the aerosol concentration is determined upon inspiration and expiration. The resulting difference is attributed to aerosol deposition in the subject's airways. Differing levels of aerosol deposition as between subjects may be used, for example, as an indication of increased airway obstruction, which is known to cause enhanced aerosol deposition. This technique, however, is relatively insensitive to small variations in pulmonary function, and hence has limited applications. In addition, it appears that the accuracy of the data derived from the single breath method may be rendered inaccurate due to effects of aerosol dilution, as described hereinafter. The prior art single aerosol deposition technique is disclosed, for example, in Distribution of Aerosol Particles in Exhaled Air, Muir, Journal of Applied Physiology, Vol. 23, No. 2, 1967, The Effect of Airways Obstruction on the Single Breath Aerosol Curve, Muir, as appearing in Airway Dynamics by Bouhys, 1970 Edition, pp. 319–325, and Aerosol Transport in the Human Lung From Analysis of Single Breaths, Taulbee et al., Journal of Applied Physiology, Vol. 44, No. 5, pp. 803–812, 1978.

Evaluation of pulmonary function by analysis of aerosol deposition data has also been carried out for single breaths by scanning the lungs after inhalation of a radioactive aerosol. Such studies are described, for example, in Early Detection of Chronic Obstructive Pulmonary Disease Using Radionuclide Lung-Imaging Procedures, Taplin, et al., Chest, Vol. 71, pp. 567–575, 1977, and Imaging Sites of Airway Obstruction and Measuring the Functional Responses to Bronchodilator Treatment in Asthma, Chopra, et al., Thorax, Vol. 34, pp. 493–500, 1979. The obvious disadvantage of this technique is that due to effects of radiation exposure, it cannot be repeated to follow serial changes after therapeutic intervention.

The prior art also recognizes that accumulated secretions in the airways may result in a two phase gas-liquid flow. Resistance to Two-Phase Gas-Liquid Flow in Airways, Clarke et al., Journal of Applied Physiology, Vol. 29, No. 4, 1970. However, the effect of this phenomenon on aerosol deposition has not heretofore been studied.

DISCLOSURE OF THE INVENTION

In accordance with the method of the present invention, airway function analysis is based on interpretation of aerosol concentration data generated during re-breathing of aerosol from a closed system. The method provides a highly sensitive indicator of airway function. The data generated by the method may be compared in several different ways. In one technique, the number of breaths required to deposit 90% of the initial aerosol concentration in the subject's airway is used. In another, the slope of the aerosol disappearance curve over a plurality of breaths is used. In either event, by comparing the results among different subjects, clinically useful information may be obtained. For example, the method may be used to evaluate the re-distribution of secretions with various types of therapeutic intervention, such as chest physiotherapy, expectorant agents, and mucolytic agents. Consequently, the method may be used to evaluate the efficacy of such therapeutic interventions.

Further aspects and advantages of the method in accordance with the present invention will be more fully apparent from the following detailed description and annexed drawings.

BRIEF DESCRIPTION OF THE DRAWINGS

In the drawings:

FIG. 1 is a diagrammatic representation of an apparatus for practicing the method of the present invention;

FIG. 2 is a semilogarithmic plot of aerosol disappearance in a normal subject ($FEV_{1.0}$=84% predicted normal) breathing 1.0 um MMAD aerosol at a 500 ml tidal volume and a frequency of 30 breaths per minute;

FIG. 3 is a semilogarithmic plot of aerosol disappearance in a patient with chronic simple bronchitis ($FEV_{1.0}$=83% predicted normal) breathing 1.0 um MMAD aerosol at a 500 ml tidal volume and a frequency of 30 breaths per minute;

FIG. 4 is a plot of aerosol disappearance slope against $FEV_{1.0}$% predicted normal for breathing 1.0 um MMAD aerosol at 500 ml tidal volume and 30 breaths per minute;

FIG. 5 is a plot of aerosol disappearance slope against airway resistance for breathing 1.0 um MMAD aerosol at 500 ml tidal volume and 30 breaths per minute;

FIG. 6 is a plot of aerosol disappearance slope against $FEV_{1.0}$% predicted normal for breathing 2.5 um MMAD aerosol at 500 ml tidal volume and 30 breaths per minute; and FIG. 7 is a plot of aerosol disappearance slope against airway resistance for breathing 2.5 um MMAD aerosol at 500 ml tidal volume and 30 breaths per minute.

BEST MODE FOR CARRYING OUT THE INVENTION

Apparatus for practicing the method of the present invention is diagrammatically illustrated in FIG. 1 and generally designated by the reference numeral 10. In practicing the method, monodisperse aerosol droplets are used. Aerosols of di(2-ethyl hexyl)sebacate as generated from a LaMer-Sinclair apparatus have been employed. Di(2-ethyl hexyl)sebacate is a bland, non-hygroscopic, oily liquid with a low vapor pressure at body temperature, and its use in aerosol deposition studies is well known. The generation of such aerosols by employing the LaMer-Sinclair apparatus is also well known, and described, for example, in Light Scattering as a Measure of Particle Size in Aerosols, Sinclair and LaMer, Chemical Reviews, 1949, Vo. 44, pp. 245–257. In lieu of Di(2-ethyl hexyl)sebacate, aerosols formed from polystyrene latex or Teflon particles may be used. Again, the formation of aerosols from such particles is known to the skilled art worker.

Typically, aerosol sizes of 1.0 and 2.5 micron mass median aerodynamic diameter (MMAD) having a geometric standard deviation less than 1.2 are used. Once generated, they are diluted with filtered air to a final concentration of approximately $10^4$ particles per cubic centimeter. The aerosol is then introduced, as by a syringe, into a 0.5 liter collapsible plastic reservoir bag 12, this volume being chosen based on the observation that subjects with chronic obstructive bronchitis cannot perform the required re-breathing manuever with high volumes at the respiratory rates of interest.

As shown in FIG. 1, an aerosol detection module 14 is connected on one side to the opening of bag 12 and at the other side to a mouthpiece 16 through which a subject 18 inhales and exhales the aerosol from bag 12. Consequently, as the subject inspires, the contents of bag 12 pass through the module 14 into mouthpiece 16, and as the subject expires, the expirate passes through the module 14 back toward the bag. The detection module 14 is included for continuously measuring the aerosol concentration in the module in order that the drop in aerosol concentration with each breath may be determined. The use of such a detection module 14 is known in the art in connection with single breath aerosol deposition studies and is disclosed, for example, in The Deposition of 0.4 μm Diameter Aerosols in the Lungs of Man, Muir and Davies, Annals of Occupational Hygiene, Vol. 10, pp. 161–174. Suffice it to say that in the detection module 14, the aerosol passes through a light scattering cell thereby interrupting a light beam from a source 20. A portion of the scattered light impinges on a photomultiplier tube 22 positioned at a right angle to the light beam, the amount of light reaching the photomultiplier being dependent on the aerosol concentration in the chamber 14. In one study, a high intensity tungsten lamp, General Electric #2331, Cleveland, Ohio, was used for the light source, and a photomultiplier tube, Model 9798B as manufactured by EMI-Gencom, Inc., Plainview, N.Y., was used as the detector. The output from the photomultiplier is preferably amplified by a picoammeter 24 with a high level output, driving an integrated circuit DC amplifer 26. The response of the foregoing aerosol concentration detector is flow independent and linear with aerosol concentrations ranging from 0 to $10^5$ particles per cubic centimeter. The aerosol concentration as represented at the output of the DC amplifier 26 was continuously recorded both on a strip chart recorder 28 and a digital computer 30, the latter comprising the Model S110 as manufactured by the Harris Corporation of Melbourne, Fla.

To insure that the subject 18 breathes through the mouthpiece 16, the subject may be fitted with a nose clip (not shown). To insure uniformity between breaths, subjects may be trained to match their breathing pattern to the sounds of a Satter Respiration Simulator, such as the Model 700 as manufactured by Somanetics of LaJolla, Calif. The subjects may also be instructed to feel the bag as an aid to perceiving the filling and emptying thereof. Also, to insure uniformity between the first breath and subsequent breaths, the initial inhalation is preferably carried out from the FRC position, i.e. at the lung volume after normal expiration. In actual studies, the subjects were capable of performing the required re-breathing manuever with ease after approximately five to ten minutes of training.

Several studies have been performed in accordance with the method of the present invention as described above. In one study, seventeen subjects were involved. Nine were life time non-smokers with a negative pulmonary history and normal spirometry, normal body plethysmography and normal single breath nitrogen test. The remaining eight subjects had chronic bronchitis and a history of chronic productive cough. Pulmonary function tests among these eight subjects were variable with $FEV_{1.0}$ ranging from 0.82 to 3.19 liters and 44% to 107% predicted normal. Two of the eight subjects with chronic bronchitis were classified as chronic simple bronchitis (normal $FEV_{1.0}$ and normal airway resistance) and six were classified as chronic obstructive bronchitis (low $FEV_{1.0}$ and/or increased airway resistance).

For each subject 18, the aerosol concentration in the chamber 14 during each inhalation was determined and expressed as a fraction of the initial inhaled concentration, i.e. the concentration during the first breath. This data was then plotted semi-logarithmically as a function of the breath number, and a least-squares linear fit was obtained. The slope of this line, which corresponded to the constant K in the equation $Y=e^{-KX}$ was calculated. In determining the slope, two satisfactory runs for each subject were averaged. To simplify the foregoing calculations, a computer program for the computer 30 was written in Fortran 66 to perform the collection, analysis and storage of the data. For each subject, the computer sampled the aerosol concentration approximately twenty times per second through an analog to digital converter. The data was then digitally filtered using a Gaussian low-pass function having a cut off frequency of 200 Hz with a window size of eight sample points. The resulting filtered data were displayed graphically on a cathode ray oscilloscope. The program was written such that aerosol concentrations could be recalled from the memory and displayed on the graphics terminal for analysis. The computer was also programmed to display the normalized concentrations, i.e. aerosol concentration as a fraction of initial inhaled concentration, and also to compute the least squares fit and plot the result. Once this description is known, any skilled art worker can write a suitable program for accomplishing these tasks, and the program per se forms no part of the present invention.

The graph of FIG. 2 is a semilogarithmic plot of aerosol disappearance versus breath number for a normal subject breathing 1.0 μm MMAD aerosol at a tidal volume of 500 ml and a frequency of 30 breaths per minute. FIG. 3 is a plot of corresponding data for a subject with chronic simple bronchitis. As is apparent from a comparison of FIGS. 2 and 3, in the normal subject aerosol concentration was reduced by 90% after about 12 breaths, whereas in the bronchitic patient, the same level was reached after about five breaths. This was so despite comparable airway resistance, as indicated by comparable values of $FEV_{1.0}$ which, for the normal and bronchitic subjects studied, were 84% and 83% predicted normal, respectively. In the course of the studies, it was found that the number of breaths required to reduce the initial aerosol concentration by 90%, which is referred to as $N_{90}$, is a convenient way of expressing aerosol disappearance for purposes of comparison. Another useful indicator is the slope of the aerosol disappearance curves. A cumulative loss of aerosol after a specific number of breaths as a percentage of initial aerosol concentration can also be a useful indicator.

Table 1 below illustrates the aerosol disappearance slopes for all trials for the 17 subjects, at breath rates of both 10 and 30 breaths per minute, and for 1.0 and 2.5 μm MMAD aerosol sizes.

TABLE 1

Aerosol Disappearance Slopes
(Mean ± Standard Deviation)

| | 10 breaths/min | 30 breaths/min | Difference between 10 and 30 breaths/min p value |
|---|---|---|---|
| 1.0 μm MMAD | | | |
| Normals | .267 ± .059 | .128 ± .032 | <.001 |
| Bronchitics | .484 ± .142 | .284 ± .105 | <.01 |
| Difference Between Normals & Bronchitics p value | <.001 | <.001 | |
| 2.5 μm MMAD | | | |
| Normals | .753 ± .202 | .494 ± .167 | <.001 |
| Bronchitics | 1.390 ± .352 | 1.020 ± .287 | <.01 |
| Difference Between Normals & Bronchitics p value | <.001 | <.001 | |

As is apparent from Table 1, in general there was minimal scatter in the data for the two groups, normals and bronchitics, as evidenced by the low standard deviation relative to the means. The aerosol disappearance slopes for patients with chronic bronchitis evidenced greater variation when the subjects rebreathed the 2.5 μm MMAD aerosol particles at 10 breaths per minute. However, this is possibly because only three or four breaths could be analyzed due to the rapid aerosol disappearance in these subjects. In general, there was a highly significant increase in the rate of aerosol disappearance in the chronic bronchitics as compared with the normal subjects for both particle sizes and both breathing rates. For both the normal subjects and the bronchitics, the steepest disappearance slopes, i.e., fastest rate of aerosol disappearance, occurred with the larger aerosol particles and slower breathing rates.

Referring now to FIG. 4, the aerosol disappearance slopes for all subjects during breathing of 1.0 μm MMAD at a 500 ml tidal volume and a frequency of 30 breaths per minute are plotted versus $FEV_{1.0}$ percent predicted normal. FIG. 5 is a similar plot showing the aerosol disappearance slopes for all subjects during breathing of 1.0 μm MMAD at a 500 ml tidal volume and a frequency of 30 breaths per minute plotted versus airway resistance. Both $FEV_{1.0}$ and airway resistance measurements are used to evaluate the extent of airway obstruction. Consequently, the graphs of FIGS. 4 and 5 were generated to show the correlation, if any, between aerosol disappearance and airway obstruction. In FIGS. 4 and 5, the hatched area encloses the data of the normal subjects, which are depicted as solid circles. The bronchitic subjects are depicted by the open circles. As is apparent from FIGS. 4 and 5, only one bronchitic subject fell within the data of the normal group. Furthermore, the graphs show a wider scatter of aerosol disappearance slopes in bronchitics as a function of airway size. The graphs in FIGS. 6 and 7 correspond to the graphs in FIGS. 4 and 5, respectively, except that the data was accumulated during breathing of 2.5 μm MMAD aerosol. In FIGS. 6 and 7 the significance of the solid and open circles and of the hatched area is the same as in FIGS. 4 and 5. As is apparent from FIGS. 6 and 7, when the larger aerosol particles were used, two of the bronchitic subjects had values within the normal range of aerosol disappearance slopes. The lowest correlation between airway obstruction and aerosol disappearance slopes occurred during breathing of 1.0 μm MMAD aerosol at 500 ml tidal volume and a frequency of 30 breaths per minute.

From Table 1 and FIGS. 2-7 it is clear that aerosol retention within the lungs during rebreathing differs both quantitatively and qualitatively in subjects with chronic bronchitis as compared with normals. Specifically, more aerosol per breath is deposited in the airways of the bronchitics as compared with normal subjects. This result is not surprising and is consistent with findings made by others utilizing a single breath technique with subjects having bronchial asthma, chronic bronchitis and pumonary emphysema.

However, the data described above as recorded in accordance with the method of the present invention demonstrates a lack of correlation for the bronchitic subjects between aerosol disappearance and airway obstruction as determined both by $FEV_{1.0}$ and airway resistance. This indicates that a reduction in airway size is not the sole factor contributing to the difference in the aerosol disappearance data for normal subjects and bronchitics.

It is generally known that altered aerosol deposition in subjects with pulmonary disease is attributable to two factors, namely, altered breathing patterns or variations in airways size and geometry. In the study described above, tidal volume and respiratory rate were controlled to eliminate variations in breathing patterns as a factor. It appears, therefore, that the different aerosol deposition data observed for the bronchitic subjects, as compared with the normals, was due to changes in airway dimensions in the bronchitics.

One possible explanation for the lack of correlation between aerosol disappearance and airway obstruction in the bronchitics is the accumulation of secretions in the airways. In one form, secretions may occur as focal accumulations. The effect of this was studied experimentally with glass tubes simulating the airways for different types of focal constrictions. This produced marked amplification of aerosol deposition just beyond the focal constriction resulting from turbulent impaction of the aerosol particles. However, the focal constriction also produced a proportionally greater increase in airway resistance than aerosol deposition. Accordingly, the phenomenon of focal accumulation of secretions does not explain the large increase in aerosol disappearance for the bronchitics which were observed in the study despite only nominal increases in airway resistance. The effect of oscillatory motion of airway wall on aerosol deposition was also studied experimentally using a vibrating compliant tube wall fabricated from a glass tube having a flexible section of thin rubber latex. Our experimental study did indicate that with oscillatory motion of airway wall, the aerosol deposition rate shows a proportionally greater increase than mean airway resistance. However, a low frequency oscillatory motion of airway walls due to the periodic nature of breathing and cardiac oscillations would not differ among subjects, and hence this too does not explain the lack of correlation between aerosol deposition and airway obstruction in the bronchitics.

Based on experimental models, it now appears that the lack of correlation between aerosol disappearance and airway obstruction in bronchitics may be caused by accumulation of secretions lining the walls of the airways in the bronchitics. Thus, it appears that when the airways are lined with secretions, the interaction between the secretions and the inhaled air may result in a form of two-phase gas-liquid pumping which produces marked wave-like and slug motion of the secretions, localized turbulence of air flow, and enhanced aerosol deposition to a much greater extent than the rise in mean airway resistance resulting from the secretions. This is to be contrasted with a focal airway constriction as discussed above. As noted, such focal constrictions produce a greater rise in airway resistance than aerosol deposition.

The conclusion that secretions lining the airways result in a proportionally greater increase in aerosol deposition than airway obstruction has been verified in connection with experiments performed on sheep. During these experiments, human airway secretions and viscoelastic polymer solutions having similar rheologic properties to human sputum were transferred to the airways of sheep. Both aerosol disappearance rates and airway obstruction were monitored. The results confirmed the conclusion that the secretions produce a proportionally greater increase in aerosol deposition than airway obstruction.

Since secretions lining the airways increase the aerosol deposition rate to a greater extent than would be expected by virtue of the increased airway resistance caused by the reduction in airway diameter resulting from such secretions, then the method of the present invention may be utilized to evaluate the redistribution (i.e. removal or lessening) of secretions resulting from therapeutic intervention. For example, various procedures and drugs, such as chest physiotherapy, mucolytic agents and expectorant agents have little or no effect on pulmonary mechanics, i.e., they do not significantly alter airway resistance. Accordingly, if a subject exhibits an abnormally steep aerosol disappearance curve which is converted to a slower, more normal curve after therapeutic intervention, then it may be assumed that the resulting decrease in the aerosol disappearance rate is due to a redistribution of secretions within the airways. Clearly, this provides the method of the present invention with significant applications for evaluating the efficacy of such therapies.

A study was also conducted to specifically determine whether chest physiotherapy causes a shift to more normal aerosol deposition rates in chronic bronchitics with productive cough. This study was conducted with fourteen subjects and using an aerosol of 1.0 m MMAD at 30 breaths per minute from a 500 ml reservoir. The chest physiotherapy consisted of a postural drainage with manual or mechanical percussion in six body positions followed by vibration during purse lip breathing on exhalation three times and one augmented cough. The resulting data indicated a rise of $N_{90}$ after chest physiotherapy without any corresponding change in pulmonary mechanics. This indicates that chest physiotherapy results in a redistribution of secretions. In another study, the aerosol disappearance data generated in accordance with the present invention was found sufficient to distinguish between normal subjects and smokers without any evidence of small airway disease as determined by conventional pulmonary function tests. In fact, the data was sufficient to make this distinction after only four breaths.

In general, the rebreathing technique in accordance with the method of the present invention exhibits superior sensitivity over the single breath technique of the prior art. Thus, if analysis is based on a single breath, variations in the aerosol deposition rate as between normal and abnormals may be masked. For example, if analysis is based on a single breath, less recovery of aerosol from that breath would be expected in subjects with larger functional residual capacities by virtue of aerosol dilution. However, when the rebreathing method of the present invention is employed, the disappearance slope and $N_{90}$ is calculated over several breaths, and dilution of aerosol becomes less important. This is true so long as there is no significant trapping of aerosol within poorly ventilated spaces in the lung, and the absence of such trapping has been supported by the simultaneous analysis of helium wash-in curves in accordance with techniques known to those skilled in the art. Consequently, by using the rebreathing technique of the present invention, differences in aerosol deposition between different subjects may be more accurately determined. In the single breath method data analysis is cumbersome because it requires an accurate integration of aerosol the concentration curve to determine the total aerosol recovery in an expired volume. The rebreathing method is straightforward, requires no calibration, no corrective factors or any other unproven assumptions so that reliable quantitative data can be obtained. Considering that the method of the present invention is highly sensitive to minor variations in pulmonary function, once this description is known those skilled in the art will undoubtedly conceive numerous applications for the inventive method other than those described above.

While we have herein shown and described the preferred method in accordance with the present invention, and have suggested certain changes and modifications thereto, the above description should be construed as illustrative and not in a limiting sense, the scope of the invention being defined by the following claims.

We claim:

1. A method for determining a subject's airway function as affected by airway cross-sectional dimensions and/or retention of tracheobroncheal secretions, comprising:
   said subject re-breathing an inert aerosol from a closed system;
   determining the aerosol concentration in said closed system during each of a plurality of breaths;
   comparing said aerosol concentration determination after each of said plurality of breaths with a predetermined aerosol concentration value to identify differences therebetween, wherein identified differences indicating enhanced aerosol deposition signify airway narrowing and/or an increase in accumulated airway secretions.

2. A method in accordance with claim 1 wherein said predetermined aerosol concentration value comprises a predicted value for said subject.

3. A method in accordance with claim 1 wherein said predetermined aerosol concentration value comprises a measurement obtained from said subject for a corresponding one of a plurality of breaths during a prior determination of the subject's airway function in accordance with said method.

4. A method in accordance with claim 3, further comprising measuring the cross-sectional dimensions of the subject's airway, and comparing said measured airway cross-sectional dimensions with the airway cross-sectional dimensions measured for said subject during said prior determination of the subject's airway function in accordance with said method, whereby identified differences indicating enhanced airway deposition accompanied by no substantial change in said measured airway cross-sectional dimensions signify an increase in accumulated airway secretions.

5. A method in accordance with claim 1 wherein said subject re-breathing and said determining of aerosol concentration is continued for a plurality of breaths until the aerosol concentration is determined to be no greater than approximately ten percent of the aerosol concentration in said closed system prior to the subject's first breath of the inert aerosol.

* * * * *